United States Patent [19]

Cho et al.

[11] Patent Number: 5,270,180
[45] Date of Patent: Dec. 14, 1993

[54] METHOD FOR THE PRODUCTION OF SALMON GROWTH HORMONE USING A SYNTHETIC GENE

[75] Inventors: Joong M. Cho, Seoul; Tae H. Lee, Daejeon; Hyun H. Chung, Seoul; Yong B. Lee, Daejeon; Tae G. Lee, Seoul; Young W. Park; Kyu B. Han, both of Daejeon, all of Rep. of Korea

[73] Assignee: Lucky, Ltd., Seoul, Rep. of Korea

[21] Appl. No.: 641,817

[22] Filed: Jan. 16, 1991

Related U.S. Application Data

[63] Continuation of Ser. No. 465,521, Jan. 17, 1990, abandoned, which is a continuation of Ser. No. 238,347, Aug. 16, 1988, filed as PCT/KR87/00014, Dec. 28, 1987, abandoned.

[30] Foreign Application Priority Data

Dec. 31, 1986 [KR] Rep. of Korea ............. 86-11708
Dec. 31, 1986 [KR] Rep. of Korea ............. 86-11709

[51] Int. Cl.$^5$ ............. C12P 21/02; C12N 1/21; C12N 1/15
[52] U.S. Cl. ............. 435/69.4; 435/69.1; 435/69.7; 435/69.8; 435/172.3; 435/320.1; 435/252.3; 435/252.33; 435/254.2; 536/23.51; 536/24.2; 536/24.1; 935/9; 935/13; 935/29; 935/28; 935/27; 935/33; 935/37; 935/38; 935/69; 935/73
[58] Field of Search ............. 435/69.1, 69.4, 91, 435/172.3, 320.1, 252.33, 254; 536/27, 23.51, 24.2, 24.1; 935/13, 28, 29, 56, 69, 73

[56] References Cited

U.S. PATENT DOCUMENTS

| | | | |
|---|---|---|---|
| 4,443,539 | 4/1984 | Fraser et al. ............. | 435/69.4 |
| 4,738,921 | 4/1988 | Belagaje et al. ............. | 436/69.7 |
| 4,849,359 | 7/1989 | Sekine et al. ............. | 435/252.33 |
| 4,880,734 | 11/1989 | Burke et al. ............. | 435/69.1 |

FOREIGN PATENT DOCUMENTS 0111814 6/1984 European Pat. Off. .
0166444 1/1986 European Pat. Off. .
0209068 1/1987 European Pat. Off. .

OTHER PUBLICATIONS

Pharmacia P.L Biochemicals Catalog 1984, p. 29.
Difco Manual (10th edition) 1984 Difco Laboratories, Detroit Michigan. pp. 1135-1138.
Strathem et al (eds.) 1981 in: *The Molecular Biology of the Yeast Saccharomyces.*, Life Cycle and Inheritance, Cold Spring Harbor Laboratory, Cold Spring Harbor, New York p. 458.
Yeast, Table of Contents, vol. 2(1) and vol. 2(2).
Sekine et al. (1985) Proc. Natl. Acad. Sci. USA 82, 4306-4310.
Pharmacia Catalog (1984) pp. 58-59.
Heron, E. J. (1984) Am. Biotechnol. Lab. (Sep. 1984).
Hallewell et al. (1985) Nuc. Acids Res. 13, 2017-2034.
Hinnen et al. (1978) Proc. Natl. Acad. Sci. USA 75, 1929-1933.
Broach et al. (1980) Cell 21, 501-508.
Russell et al. (1983) J. Biol. Chem. 258, 2674-2682.
Beier et al. (1982) Nature 300, 724-728.
Brake et al. (1984) Proc. Natl. Acad. Sci. USA 81, 4642-4646.
Maniatis et al. (1982) *Molecular Cloning: A Laboratory Manual* pp. 404-433.

Primary Examiner—Christopher S. F. Low
Attorney, Agent, or Firm—Birch, Stewart, Kolasch & Birch

[57] ABSTRACT

High protein content feed or hormonal steroids have been added to fish feed in order to elevate the efficiency of the feed. However, the steroids remain in the fish and may be detrimental to those who eat the fish. The invention relates to a method for the production of salmon growth hormone, which enhances the efficiency of the feed without the above side effects, using a synthetic gene in yeast or *E.coli*. It has been found that salmon growth hormone may be produced economically and in bulk in yeast or *E.coli* by gene manipulation technology.

4 Claims, 8 Drawing Sheets

FIG. 1

```
SGH(5' - 3'):  GENE SEQUENCE

U1:   TATGATCGAAAATCAGCGTTTATTCAACATTGCAGTTT     (38mer)
    U2:   CTAGAGTTCAACACTTGCACTTGTTGGCTCAAAAGATGTTCAACGACT  (48mer)
    U3:   TCGACGGTACCTTGTTGCCAGACGAAAGAAGACAATTGAACA  (42mer)
    U4:   AGATTTCTTGTTGGACTTCTGTAACTCTGACTCTATTGTTT  (42mer)
    U5:   CTCCAGTTGACAAGTACGAAACCCAAAAGTCTTCTGTTTTGA  (42mer)
    U6:   AGTTGTTGTACATTTCTTTCAGATTGATTGAATCTTGGGAAT  (42mer)
    U7:   ACCCATCTCAAACCTTGATTATTTCGAATTCTTTGATGGTTA  (42mer)
    U8:   GAAACGCTAACCAAATTTCTGAAAAGCTTTCTGACTTGAAGG  (42mer)
    U9:   TTGGTATTAACTTGTTGATTACCGGTTCTCAAGACGGTGTTT  (42mer)
   U10:   TGTCTTTGGACGACAACGACTCTCAACAATTGCCACCATACG  (42mer)
   U11:   GTAACTACTACCAAAACTTGGGTGGTGACGGTAACGTTAGAA  (42mer)
   U12:   GAAACTACCAATTGTTGGCTTGTTTCAAGAAGGACATGCACA  (42mer)
   U13:   AGGTTGAAACCTACTTGACCGTTGCTAAGTGTAGAAAGTCTT  (42mer)
   U14:   TGGAAGCTAACTGTACCTTGTAG                    (23mer)
    L1:   CTAGAAACTGCAATGTTGAATAAACGCTGATTTTCGATCA   (40mer)
    L2:   AGCCAACAAGTGCAAGTGTTGAACT                  (25mer)
    L3:   GTCTGGCAACAAGGTACCGTCGAAGTCGTTGAACATCTTTTG (42mer)
    L4:   ACAGAAGTCCAACAAGAAATCTTGTTCAATTGTCTTCTTTC  (42mer)
    L5:   GGTTTCGTACTTGTCAACTGGAGAAACAATAGAGTCAGAGTT (42mer)
    L6:   TCTGAAAGAAATGTACAACAACTTCAAAACAGAAGACTTTTG (42mer)
    L7:   AATAATCAAGGTTTGAGATGGGTATTCCCAAGATTCAATCAA (42mer)
    L8:   TTCAGAAATTTGGTTAGCGTTTCTAACCATCAAAGAATTCGA (42mer)
    L9:   GGTAATCAACAAGTTAATACCAACCTTCAAGTCAGAAAGCTT (42mer)
   L10:   AGAGTCGTTGTCGTCCAAAGACAAAACACCGTCTTGAGAACC (42mer)
   L11:   ACCCAAGTTTTGGTAGTAGTTACCGTATGGTGGCAATTGTTG (42mer)
   L12:   ACAAGCCAACAATTGGTAGTTTCTTCTAACGTTACCGTCACC (42mer)
   L13:   AACGGTCAAGTAGGTTTCAACCTTGTGCATGTCCTTCTTGAA (42mer)
   L14:   TCGACTACAAGGTACAGTTAGCTTCCAAAGACTTTCTACACTTAC (45mer)
```

SGH: LIGATION STRATEGY

```
                                       30
    ATC GAA AAC CAA AGA TTG TTC AAC ATT GCT GTT TCT AGA GTT
    Ile Glu Asn Gln Arg Leu Phe Asn Ile Ala Val Ser Arg Val 60                                  90
    CAA CAC TTG CAC TTG TTG GCT CAA AAG ATG TTC AAC GAC TTC GAC
    Leu His Leu Leu Ala Gln Lys Met Phe Asn Asp Phe Asp Gly Thr

120
    GGT ACC TTG TTG CCA GAC GAA AGA AGA CAA TTG AAC AAG ATT TTC
    Gln His Leu Leu Pro Asp Glu Arg Arg Gln Leu Asn Lys Ile Phe 150                                 180
    TTG TTG GAC TTC TGT AAC TCT GAC TCT ATT GTT TCT CCA GTT GAC
    Leu Leu Asp Phe Cys Asn Ser Asp Ser Ile Val Ser Pro Val Asp

210
    AAG TAC GAA ACC CAA AAG TCT TCT GTT TTG AAG TTG TTG TAC ATT
    Lys Tyr Glu Thr Gln Lys Ser Ser Val Leu Lys Leu Leu Tyr Ile 240                                 270
    TCT TTC AGA TTG ATT GAA TCT TGG GAA TAC CCA TCT CAA ACC TTG
    Ser Phe Arg Leu Ile Glu Ser Trp Glu Tyr Pro Ser Gln Thr Leu

300
    ATT ATT TCG AAT TCT TTG ATG GTT AGA AAC GCT AAC CAA ATT TCT
    Ile Ile Ser Asn Ser Leu Met Val Arg Asn Ala Asn Gln Ile Ser 330                                 360
    GAA AAG CTT TCT GAC TTG AAG GTT GGT ATT AAC TTG TTG ATT ACC
    Glu Lys Leu Ser Asp Leu Lys Val Gly Ile Asn Leu Leu Ile Thr

390
    GGT TCT CAA GAC GGT GTT TTG TCT TTG GAC GAC AAC GAC TCT CAA
    Gly Ser Gln Asp Gly Val Leu Ser Leu Asp Asp Asn Asp Ser Gln 420                                 450
    CAA TTG CCA CCA TAC GGT AAC TAC TAC CAA AAC TTG GGT GGT GAC
    Gln Leu Pro Pro Tyr Gly Asn Tyr Tyr Gln Asn Leu Gly Gly Asp

480
    GGT AAC GTT AGA AGA AAC TAC CAA TTG TTG GCT TGT TTC AAG AAG
    Gly Asn Val Arg Arg Asn Tyr Gln Leu Leu Ala Cys Phe Lys Lys 510                                 540
    GAC ATG CAC AAG GTT GAA ACC TAC TTG ACC GTT GCT AAG TGT AGA
    Asp Met His Lys Val Glu Thr Tyr Leu Thr Val Ala Lys Cys Arg

AAG TCT TTG GAA GCT AAC TGT ACC TTG
    Lys Ser Leu Glu Ala Asn Cys Thr Leu
```

*FIG. 4*

METHOD FOR THE PRODUCTION OF SALMON GROWTH HORMONE USING A SYNTHETIC GENE

This application is a continuation of application Ser. No. 07/465,521, filed Jan. 17, 1990 now abandoned, which is a continuation of application Ser. No. 07/238,347, filed Aug. 16, 1988, filed as PCT/KR87/00014, Dec. 28, 1987, now abandoned.

BACKGROUND OF THE INVENTION

The present invention relates to a method for the production of salmon growth hormone using a synthetic gene in yeast or *E. coli*.

Up to now high protein content feed or hormonal steroids have been added to the feed used at fish farms in order to elevate the efficiency of the feed. It has been found in developed nations including the U.S.A. that the steroid, however, is not metabolized immediately but remains in the fish for a long time after ingestion. The presence of the steroid is detrimental o those who eat the fish and thus prohibition of the use of these steroids has increased.

On the other hand, because salmon growth hormone does not remain inside the body of the fish after ingestion and because it has a species-specificity, as it is a protein of salmon itself, it is the most desirable material capable of increasing the efficiency of feed.

The present inventors have discovered that salmon growth hormone may be produced economically and in bulk in yeast or *E. coli* by gene manipulation technology.

SUMMARY OF THE INVENTION

One object of the present invention is to provide a method for the production of salmon growth hormone using yeast as a host for expression vectors.

The other object of the present invention is to provide a method for the production of salmon growth hormone using *E. coli* as a host for expression vectors.

Firstly, the method for the production of salmon growth hormone using yeast as a host for expression vectors comprises:

(a) synthesizing oligonucleotides having XbaI, HindIII and SalI restriction sites for manipulation of the salmon growth hormone gene (b) ligating one fragment with the XbaI/HindIII sites and the other fragment with the HindIII/SalI sites according to the ligation strategy (FIG. 3) to the plasmid PUC18, respectively, (c) religating the two cloned fragments together to the plasmid pUC18, to get a salmon growth hormone gene lacking a portion of the N-terminus, (d) inserting the partial salmon growth hormone gene and N-terminal synthetic adaptor to a plasmid consisting of a promoter and a terminator to make a cassette of promoter-salmon growth hormone with an N-terminal synthetic adaptor-terminator, (e) inserting the cassette into an *E. coli*-yeast shuttle vector for expression in yeast and (f) expressing the resultant vector in yeast cells.

The N-terminal synthetic adaptor is the following nucleotide sequence having NcoI site and XbaI site:

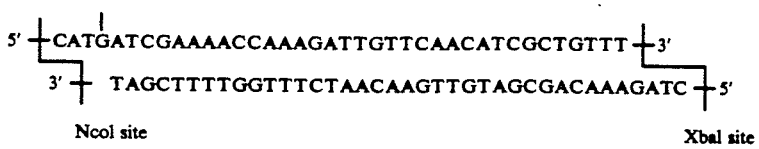

Ncol site          XbaI site

The yeast expression vector is named as pCl/1-SGH containing the cassette comprising promoter-salmon growth hormone gene with an N-terminal synthetic adaptor-terminator, a complete 2 micron circle, a Leu 2d gene and an origin of replication.

Secondly, the method for the production of salmon growth hormone in *E. coli* as a host comprises: (a) synthesizing oligonucleotides having XbaI, HindIII and SalI restriction sites for manipulation of the salmon growth hormone gene, (b) ligating the N-terminal fragment with the XbaI/HindIII sites and the C-terminal fragment with the HindIII/SalI sites according to the ligation strategy (FIG. 3) to plasmid pUCI8, respectively, (c) religating the two cloned fragments to plasmid pUC18, to get a salmon growth hormone gene lacking a portion of I5 the N-terminus, (d) inserting the partial salmon growth hormone gene and N-terminal synthetic adaptor to plasmid, pBR322, (e) ligating the obtained salmon growth hormone gene and a synthetic adaptor to the expression vector with trp promoter and (f) expressing the resultant vector with the synthetic adaptor in *E. coli*.

The N-terminal synthetic adaptor for *E. coli* expression vector is the following nucleotide sequence which has NdeI and XbaI sites and comprises an upper strand of 38 mer 5' -T ATG ATC GAA AAT CAG CGT TTA TTC AAC ATT GCA ATT T-3' and a lower strand of 40 mer 3' -AC TAG CTT TTA GTC GCA AAT AAG TTG TAA CGT CAA AGA TC-5'

The other synthetic adaptor for a partial promoter sequence is the following nucleotide sequence which has HpaI and NdeI sites and comprises an upper strand of 36 mer 5' -AAC TAG TAC GCA AGT TCA CTG AAA AAG GGT AAT ACA -3' and a lower strand of 38 mer 3' -TTG ATC ATG CGT TCA AGT GCA TTT TTC CCA TTA TGT AT-5'.

For a better understanding of the invention, reference is made to the accompanying drawings and descriptive matter in which a preferred embodiment of the invention is illustrated.

BRIEF DESCRIPTION OF THE DRAWINGS

FIG. 1 shows synthetic oligonucleotides corresponding to a salmon growth hormone gene and represented by a base sequence from the 5'-end to the 3'-end.

FIG. 4 is the base sequence and putative amino acid sequence of confirmed salmon growth hormone gene.

DETAILED DESCRIPTION OF A PREFERRED EMBODIMENT

The present inventors selected the base sequence of salmon growth hormone with amino acid codons preferentially used by yeast cells, based upon the amino acid sequence of salmon growth hormone, reported by Sekine et al. [Proc. Natl. Acad. Sci, USA 82:4308 (1985)] and the complete gene of mature salmon growth hormone was chemically synthesized using a DNA synthesizer (Applied Biosystem Model 380B, USA) using phosphoramidate chemistry.

Figure 3:
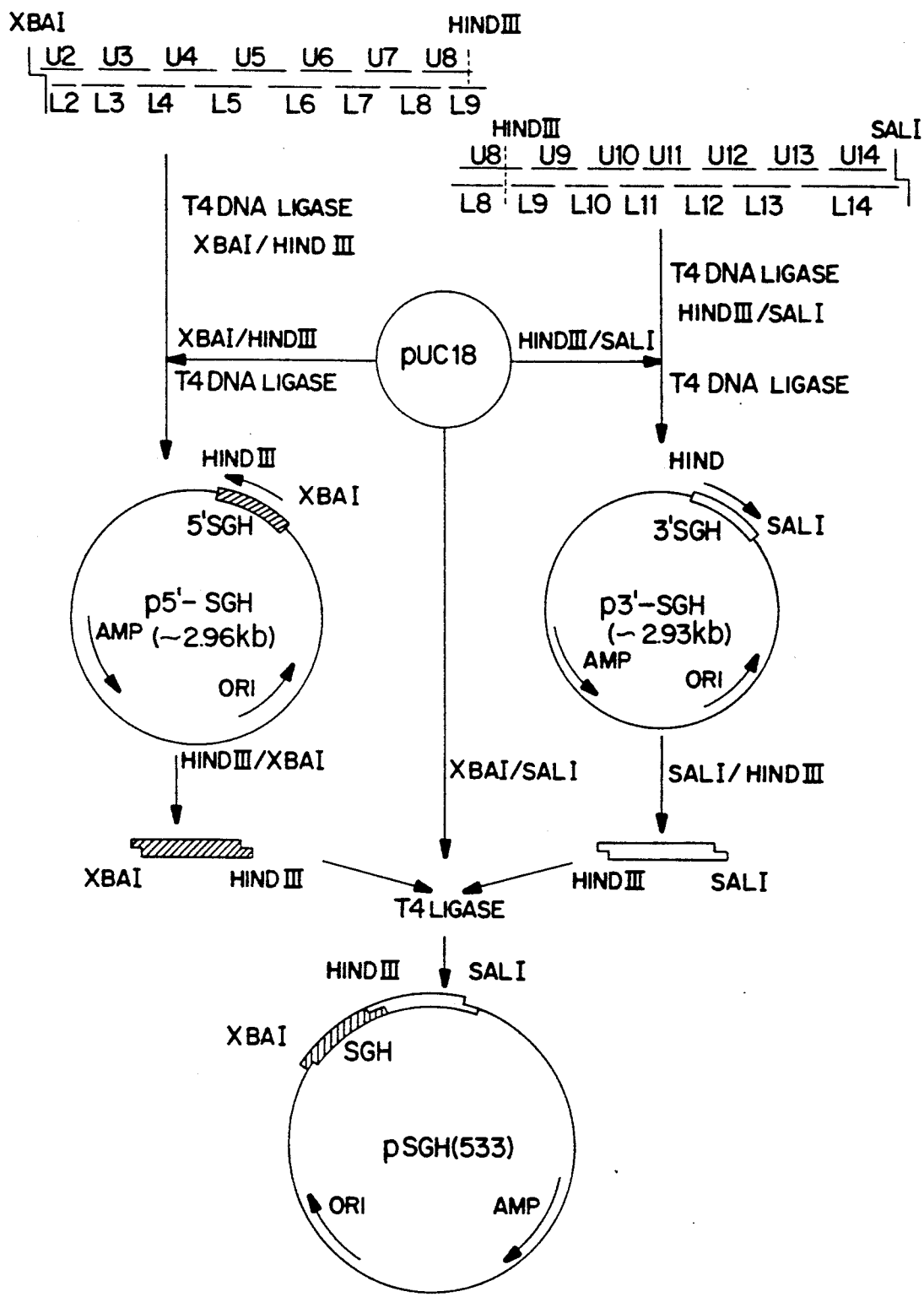
FIG. 3 is a schematic cloning process of synthetic oligonucleotides to the plasmid, pUC18.

The synthetic oligonucleotides are ligated and inserted into a plasmid vector replicatable in *E. coli*, pUCI8 [Norrander, J. et al., Gene 36:101 (1983)] to produce pSGH(533). This plasmid contains an XbaI/-SalI restriction fragment of 533 bp, which encodes a salmon growth hormone gene lacking the N-terminal region of the complete protein. The structure of pSGH(533) is shown in FIG. 3.

Firstly, a method for the production of salmon growth hormone in yeast cells is as follows; The XbaI-SalI insert from pSGH(533) comprising the salmon growth hormone gene lacking the N-terminal region adaptor is ligated to an adaptor having an NcoI site, an initiation codon, several amino acids of the N-terminal portion of the salmon growth hormone protein and an XbaI site. The completed SGH cDNA is then ligated to a vector having a promoter and a terminator gene that function in yeast, pBS100 [Valenzuelar, P., Yeast 2:72 (2986): Chiron Corp., Emeryville, Calif. 94608, U.S.A.]. The obtained vector is pBS-SGH.

Figure 5:
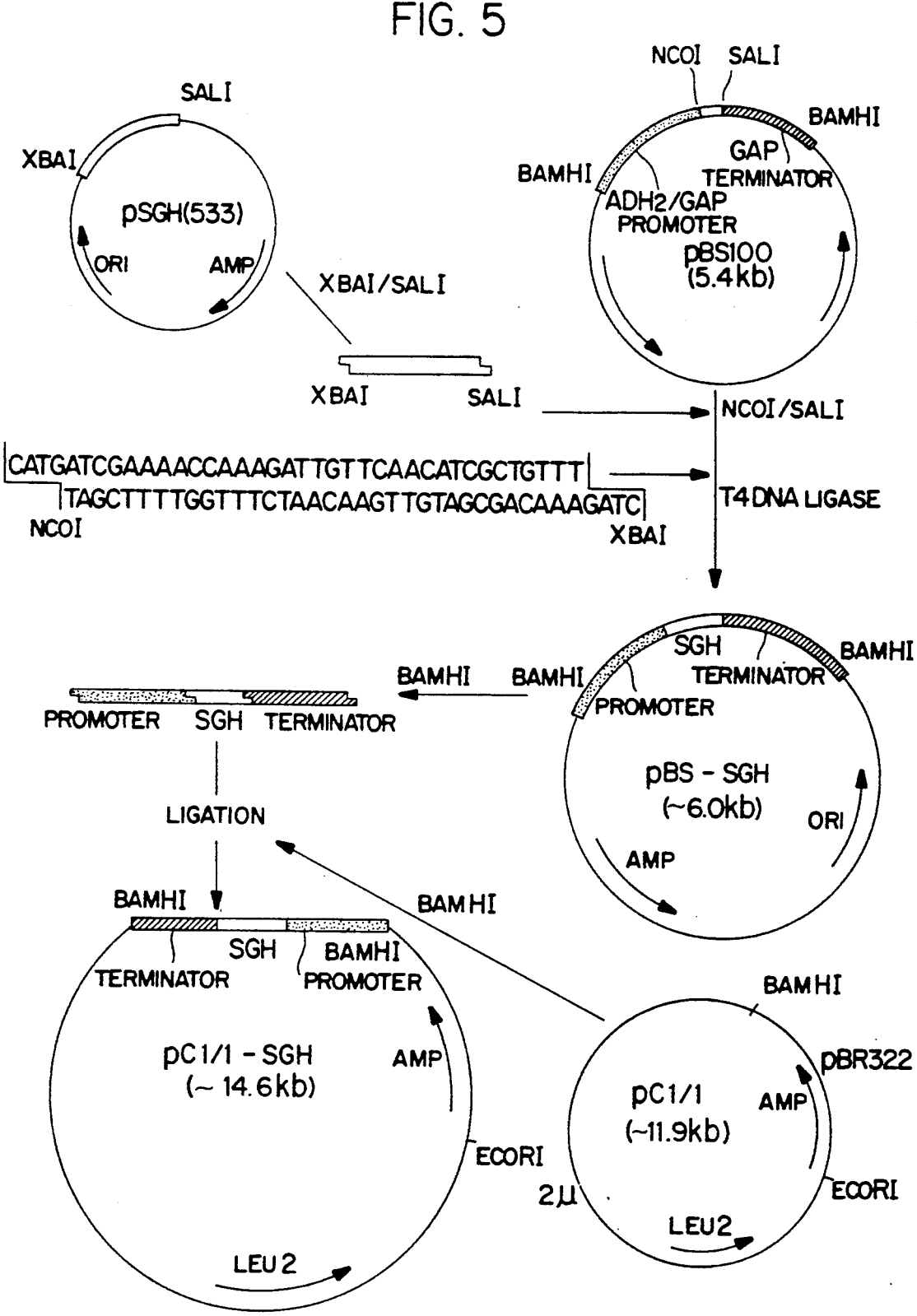
FIG. 5 is a cloning process into a yeast expression vector (pCl/1) for producing salmon growth hormone in yeast.

The vector pBS-SGH was treated with BamHI restriction enzyme to separate the BamHI fragment (about 2.7 kb) comprising the promoter, salmon growth hormone gene and terminator. The BamHI fragment is inserted into the BamHI restriction site of a yeast expression vector, pCI/1, which is capable of replication in both *E. coli* and yeast [ATCC 37115; Brake et al. Proc. Natl. Acad. Sci., USA 81:4642 (1984)] to produce pCI/I-SGH (Refer to FIG.5).

The above yeast expression vector is transformed into yeast strain DC04 [Broach, J. R. & Hicks, J. B., Cell 21, 501 (1980); Yeast Genetic Stock Center, University of California, Berkeley, U.S.A.] by the method of Hinnen et al. The transformed yeast cell wa cultured in YEPD medium comprising 2% glucose as in Example 4 for 48 hrs. When the glucose in the medium is exhausted, salmon growth hormone is induced and salmon growth hormone is obtained in a yield of about 50 mg per liter of culture at $OD_{650}=15$.

Secondly, a method for the production of salmon growth hormone in *E. coli* is as follows; The XbaI/SalI insert fragment of pSGH(533) is ligated to a synthetic adaptor designed to contain an ATG initiation codon within an NdeI restriction enzyme recognition site and which contains codons preferentially used in *E. coli*. The ligated pieces are finally ligated to the plasmid vector pBR322, which replicates in *E. coli* (Refer to Example 3).

A plasmid vector for expression of the synthetic SGH gene in *E. coli*, under the control of a trp promoter, ptrp 322, was made from the trp promoter obtained from the pDR720 plasmid (Pharmacia, Inc., Piscataway, N.J., catalog number 27-4930-01) which is similar to the pDR plasmids described by Russell and Bennett (Russell, D. R. and Bennett, G. N., Gene 20:231 (1982)). pDR720 was digested with SmaI and HindIII and the small fragment containing the trp promoter was purified. The plasmid pBR322 (commonly available) was digested with HindIII and PvuII and the large fragment containing the ampicillin resistance gene and origin of replication was purified. The two purified fragments were ligated to obtain the plasmid ptrp 322.

The NdeI/SalI restriction fragment of 571 base pairs comprising the complete growth hormone gene linked to a synthetic oligonucleotide in which the bases between the SD (Shine Dalgarno) sequence and ATG, an initiation codon, are suitably arranged in order to produce an mRNA lacking extensive secondary structure was ligated to which had been cut with HpaI and SalI restriction enzymes. After that, the resultant vector (ptrp322HSGH) was transformed into *E. coli* W3110 (ATCC 27325) (Refer to Example 3). The salmon growth hormone gene was expressed in *E. coli* by using IAA (Indole Acrylic Acid) as an inducing agent in M9 medium and salmon growth hormone was identified by means of SDS-polyacrylamide gel electrophoresis to (Refer to Example 5).

The invention is illustrated by the following Examples, which are meant to be illustrative only, and not to be understood as limiting the scope of the invention.

Example Ligation and cloning of synthetic oligonucleotides for salmon growth hormone gene.

Figure 2:
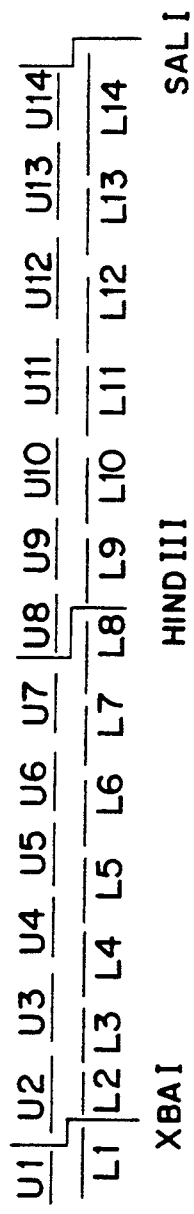
FIG. 2 is a ligation strategy of oligonucleotides in accordance with FIG. 1.

In order to obtain a complete salmon growth hormone gene from the synthetic oligonucleotides having the sequences of FIG. the ligation strategy of FIG. 2 and vector pUC18 were used.

Each oligonucleotide (U8-U14/L9-L14) corresponding to the C-terminal HindIII and SalI restriction fragments of the salmon growth hormone gene was taken in the amount of 0.05 $OD_{260}$ respectively, and then separately dried. To each dried oligonucleotide, four units of T4 polynucleotide kinase are added to a total volume of 30μl of 50 mM Tris-KCl (pH 7.5), 1 mM ATP, 1 mM DTT and 10 mM $MgCl_2$ and reacted for 30 minutes in order to phosphorylate the 5'-end residue of the oliqonucleotides.

After the oligonucelotides are pooled and treated with an equal volume of phenol and chloroform mixture (24:1, v/v), they are precipitated with ethanol. The precipitates were dissolved in 53 μl of a buffer solution comprising 60mM Tris-HCl (pH 7.5), ImM DTT and 10 mM $MgCl_2$. The solution was placed in 95° C. water bath which was then allowed to equilibrate at room temperature for 6 hrs until the temperature came to room temperature to anneal the DNA fragments.

Twenty units of T4 DNA ligase and 5 μl of 10 mM ATP were added to the annealed DNA and the ligation reaction was done at room temperature for 10 mins. This reaction solution was treated with phenol and chloroform mixture and precipitated with ethanol as described above.

Ten units each of HindIII and SalI restriction enzymes are added to the precipitate in the presence of a buffer solution comprising 60 mM Tris-HCl (pH 7.6), 10 mM $MgCl_2$ and 100 mM NaCl and reacted at 37° C. for 1 hr.

After 7% polyacrylamide gel electrophoresis, a band corresponding to 220-300 base pairs is cut from the gel. After electroelution, the DNA was dissolved in 20 μl of distilled water.

Three μl of electroeluted DNA and 10 ng of a vector, pUC18, which had been cut with HindIII and SalI restriction enzymes are ligated in the presence of the ligation solution comprising 60 mM Tris-HCl (pH 7.5), 10 mM MgCl$_2$, 1 mM ATP and 10 units of T4 DNA ligase at 14° C. for 16 hrs.

E. coli JM103 [BRL, U.S.A., Messing, J., Methods in Enzymology, 101:20 (1983)] competent cells were added to the ligation mixture and transformed according to Hanahan's method [J. Mol. Biol 118: 557 (1983)] at 37° C. overnight.

The recombinant vector, p3'-SGH was isolated from the white clonies according to the method of Birnboim and Doly [Nucleic Acid Res. 7:1513 (1979)].

On the other hand, the oligonucleotides (U1-U7/L2-L8) corresponding to the N-terminal XbaI and HindIII restriction fragments of the synthetic oligonucleotides were ligated by the same method as mentioned above and inserted to pUC18, which had been cut with XbaI and HindIII restriction enzymes, to get p5'-SGH as illustrated by FIG. 3.

Finally, the DNA sequences of p3'-SGH and p5'-SGH are confirmed by DNA sequencing using the dideoxy chain termination method [Proc. Natl. Acad. Sci. USA 74:5473, (1977)] (Refer to FIG. 4).

The HindIII/SalI restriction fragment from p3'-SGH and the XbaI/HindIII restriction fragment from p5'-SGH are isolated respectively and ligated to a vector, pUC18, cut with XbaI and SalI restriction enzymes to produce pSGH (533) (Refer to FIG. 3).

Example 2: Manipulation of synthetic salmon growth hormone gene for expression in yeast cells The salmon growth hormone gene that is the insert in pSGH(533) lacks sequences coding the amino terminus of the hormone. To provide these amino acids, an adaptor was sythesized by a DNA synthesizer. In the synthetic adaptor, and NcoI restriction enzyme site, an initiation codon and codons corresponding to NH$_2$-terminal 12 amino acids of salmon growth hormone were synthesized by selecting codons preferentially used in yeast cells (Refer to FIG. 5).

The process of cloning is as follows; pSGH(533) was treated with XbaI and SalI restriction enzymes to obtain a 533 bp restriction fragment and the fragment was isolated by agarose gel electrophoresis.

The synthetic adaptor was phosphorylated with T4 polynucleotide kinase as described previously. One μl of the phosphorylated adaptor reactant, 3 μl (30ng) of the XbaI/SalI fragment of growth hormone gene and 1 μl (7 ng) of vector pBS100 (Valenzuelar, P., Yeast 2:72 (1986)) cut with NcoI and SalI restriction enzymes were mixed together in the presence of 2 μl of distilled water and incubated at 14° C. for 16 hrs. As mentioned in Example 1, the ligation mixture was transformed into E. coli HB101 (ATCC 33694) and a recombinant plasmid pBS-SGH comprising a promoter, the complete salmon growth hormone gene and a terminator for expression in yeast was obtained.

The above mentioned vector, pBS100, contains a hybrid promoter consisting of elements of the alcohol dehydrogenase II promoter and glyceraldehyde 3'-phosphate dehydrogenase promoter.

The vector pBS-SGH was treated with BamHI restriction enzyme to separate the BamHI restriction fragment of about 2,700 bp, comprising the hybrid promoter, the salmon growth hormone gene and the terminator of glyceraldehyde 3'-phosphate dehydrogenase. The BamHI restriction fragment was inserted into the BamHI restriction site of the vector for yeast expression, pCI/l(ATCC 37115), to obtain pCl/1-SGH (Refer to FIG. 5).

Ten μg of pCI/1-SGH gene was transformed into yeast strain DC04 [Yeast Genetic Stock Center, University of California, Berkeley, U.S.A., Broach, J. R. & Hicks, J. B., Cell 21:501 (1980)] according to the method of Hinnen [Proc. Natl. Acad. Sci. USA 75:1929 (1978) and plated on agar plates lacking leucine, such plates comprising 6.7 g of Yeast Nitrogen Base without amino acids, 182 g of sorbitol 2% glucose, 0.25 g of Leu- supplements and 20 g of Bactoagar per liter.

Recombinant clones containing salmon growth hormone gene appeared 3 to 5 days after transformation.

Example 3: Cloning of the complete salmon growth hormone gene in an E. coli expression vector DNA sequences corresponding to NH$_2$-terminal amino acids of the complete salmon growth hormone gene were selected incorporating codons preferentially used in E. coli.

An NdeI and XbaI adaptor consisting of an upper strand 38mer 5'-T ATG ATC GAA AAT CAG CGT TTA TTC AAC ATT GCA GTT T-3' and a lower strand 40 mer 3'-AC TAG CTT TTA GTC GCA AAT AAG TTG TAA CGT CAA AGA TC-5' were synthesized. The XbaI/SalI fragment of 533 base pairs separated from pSGH and the synthetic adaptor were inserted into a vector for E. coli, pBR322 [ATCC 37017], which had been cut with NdeI and SalI restriction enzymes, to obtain plasmid pB SGH comprising the complete salmon growth hormone gene (Refer to FIG. 6).

An expression vector with trp promoter, ptrp322 was cut with HpaI and SalI restriction enzymes. The fragment of 2.3 Kb was electroeluted after purification by agarose gel electrophoresis and precipitated with ethanol.

The pBR SGH described above wa treated with NdeI and SalI restriction enzymes to obtain a fragment of 571 bp. A synthetic adaptor was designed so that a 9 base sequence was present between the SD sequence (5'-AAGG-3') of the trp promoter and the initiation codon of the salmon growth hormone gene and the mRNA corresponding to the region does not form extensive secondary structure. An adaptor consisting of an upper strand 36 mer 5'AAC TAG TAC GCA AGT TCA CGT AAA AAG GGT AAT ACA-3' and a lower strand 38 mer 3'-TTG ATC ATG CGT TCA AGT GCA TTT TTC CCA TTA TGT AT-5' was designed so that a NdeI end is adapted to a HpaI end.

The NdeI/SalI restriction fragment of 571 bp and the synthetic adaptor were ligated to ptrp322, which had been cut with HpaI and SalI restriction enzymes.

Figure 6:
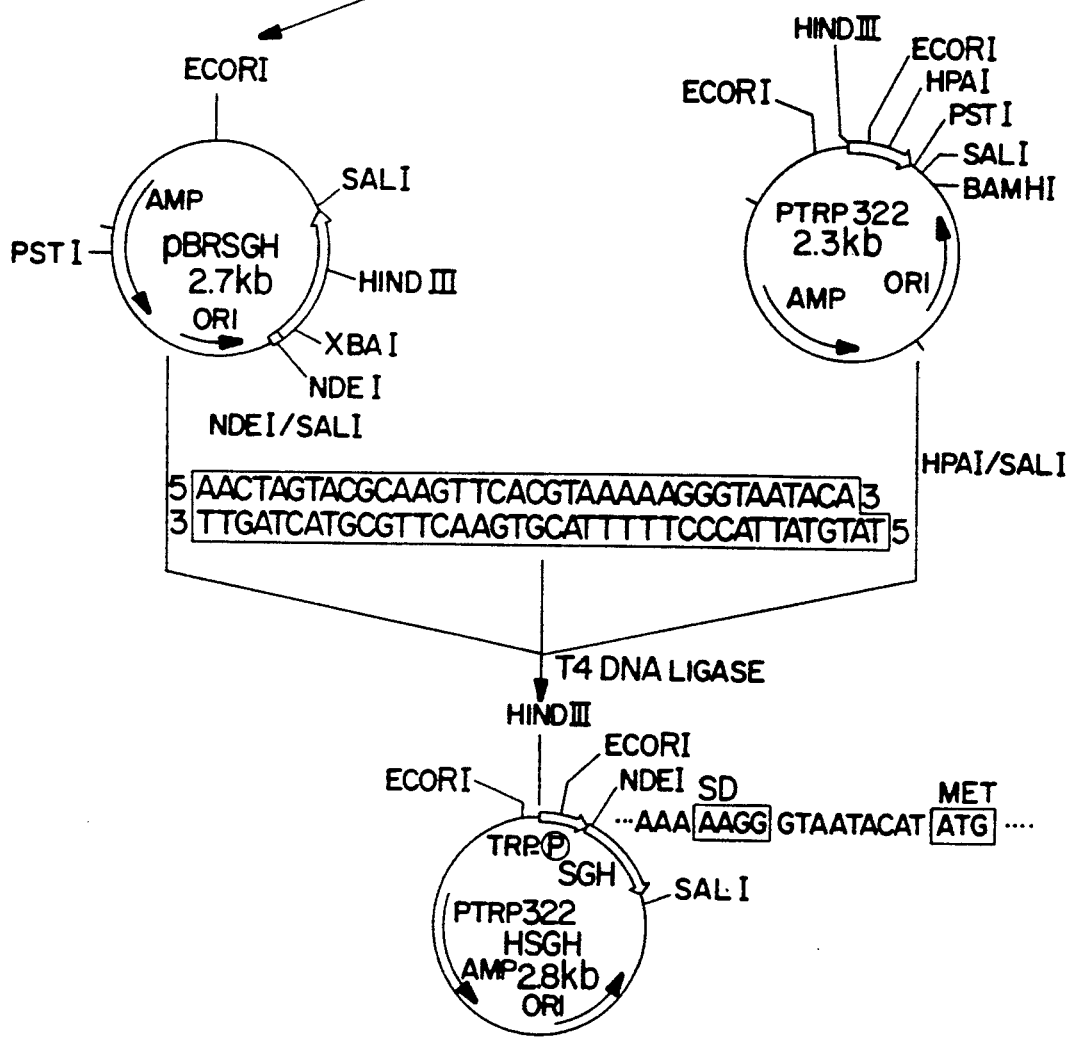
FIG. 6 is a cloning strategy for expression of salmon growth hormone gene in *E. coli*.

E. coli HB101 (ATCC 33694) was transformed to obtain a recombinant clone containing the salmon growth hormone gene linked to the trp promoter, which is called ptrp 322 HSGH (Refer to FIG. 6). It is again transformed into a bacterial host for expression, E. coli, W3110 (ATCC 27325).

Example 4: Cultivation for producing salmon growth hormone in yeast cells and its identification Each 3 ml of yeast cells transformed with vector pCl/1-SGH was cultured in a culture medium without leucine (6.7 g of Yeast Nitrogen Base without amino acids, 0.25 g of Leu- supplements and 6% glucose per liter of culture medium) at 30° C. for 24 hrs. YEpD culture medium (100 ml) comprising 2% peptone, 1% yeast extract and 2% glucose was inoculated with 1 ml of the overnight culture and cultured at 30° C. for 24 hrs. 4.0 ml of ethanol was added thereto and the solution was further cultured for 24 hrs.

The resultant $OD_{650}$ was about 40. A sample of culture representing 10 $OD_{650}$ units was taken and centrifuged. It was dissolved in 400 μl of a buffer solution containing 10 mM Tris-HCl (pH 7.5), mM EDTA, 2 mM phenyl methyl sulfonyl fluoride (PMSF). The same volume of 8 M urea and glass beads with a diameter of 0.45 mm were added thereto and shaken vigorously. After rupturing the cell wall and allowing the salmon growth hormone to elute into the buffer solution, 4 μl of eluted solution was examined by electrophoresis on a 12.5% SDS polyacrylamide gel.

Figure 7:
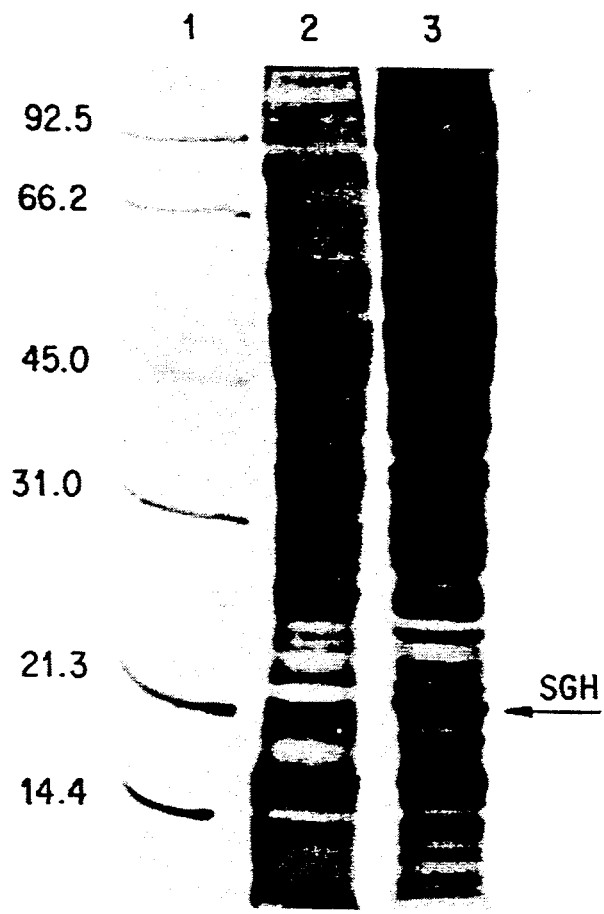
FIG. 7 are the results confirmed by SDS-polyacrylamide gel electrophoresis of salmon growth hormone produced in yeast cells.

The results are represented in FIG. 7;

Lane 1 represents protein standard Molecular weight (Bio-Rad).

Lane 2 represents all the cellular proteins of yeast [cell] transformed with vector pCl/1 lacking the salmon growth hormone gene.

Lane 3 represents all of the cellular proteins of yeast transformed with vector pCl/1-SGH including the salmon growth hormone gene.

As shown in lane 3 of FIG. 7, the salmon growth hormone appears as a band abut 22 kD in an amount corresponding to 5% of the total proteins as determined by densitometric scanning of the gel.

Peptid sequencing of the purified salmon growth hormone showed that it is mature salmon growth hormone, having isoleucine as the amino-terminal codon.

Example 5: High-level expression of salmon growth hormone gene in *E. coli* W3110 and confirmation by SDS-polyacrylamide gel electrophoresis

*E. coli* W3110, containing the expression vector ptrp 322 HSGH was cultured in LB medium containing 40 μg/ml of ampicillin at 37° C. for 16 hrs. and then inoculated into M9 medium. When $OD_{650}$ reached 0.5, 60 μg/ml of IAA (Indole Acrylic Acid) was added and the culture continued at 37° C. for 24 hrs. An amount of the cultured bacteria dissolved in 100 μl of Laemmli sample buffer [Laemmli, D. K., Nature 227:680 (1970)]. The solution was heated at 100° C. for 5 mins and then 10 μl of it was applied to a 12.5% SDS polyacrylamide electrophoresis gel.

Figure 8:
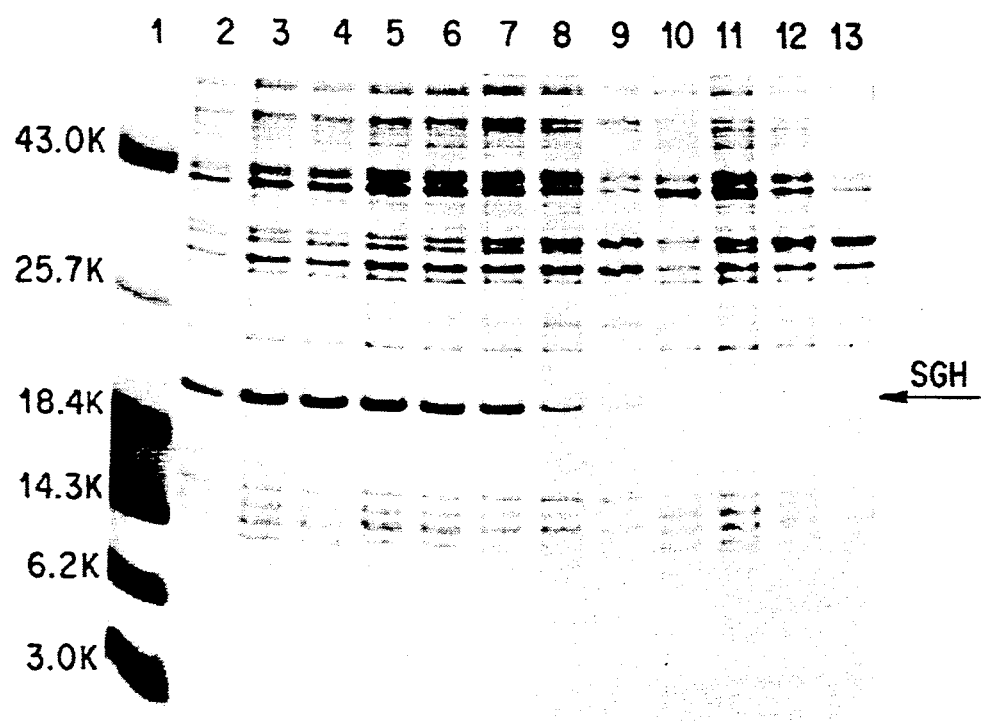
FIG. 8 are the results confirmed by SDS-polyacrylamide gel electrophoresis of salmon growth hormone produced in *E. coli*.

The results are represented in FIG. 8;

Lane 1 represents BRL low molecular weight markers.

Lanes 2-9 represent the results of strain W3110 with the salmon growth hormone gene (contained in plasmid ptrp 322 HSGH) induced by IAA.

Lanes 10-13 represent the results of strain W3110 without the salmon growth hormone gene (vector ptrp 322 only) induced by IAA.

As shown in FIG. 8, a band of 22 kD which can not be seen in ptrp 322-W3110 without salmon growth hormone gene appears in ptrp322 SGH-W3110. This band is present in an amount of more than 20% of total *E. coli* proteins as determined by desitometric scanning of the gel.

M9 medium comprises 40mM $K_2HPO_4$, 8.5 mM NaCl, 18.7mM $NH_4Cl$, 1 mM $MgSCO_4$, 0.1 mM $CaCl_2$, 10 μg/ml Vit $B_1$, 0.4% Casamino acid, 1% glucose and 40 μ/ml of ampicillin.

We claim:

1. A process for the production of salmon growth hormone by culture of a eukaryotic microorganism expressing said salmon growth hormone from a recombinant plasmid, the improvement which comprises:
   1) producing a yeast strain containing a salmon growth hormone gene by transforming said yeast strain with the vector pCl/1-SGH, said vector being described in FIG. 5;
   2) culturing said transformed yeast in medium comprising Yeast Nitrogen Base without amino acids, Leu- supplements and glucose;
   3) diluting the culture of step 2 into a medium comprising peptone, yeast extract and glucose and further culturing the cells;
   4) adding to the culture ethanol and further incubating the cells; and
   5) separating the yeast cells from the culture medium and collecting the salmon growth hormone from within the cells, wherein said salmon growth hormone is obtained in a yield of at least 5% of total yeast protein.

2. The process of claim 1, wherein the yeast strain that is transformed is DCO4.

3. A process for the production of salmon growth hormone by culture of a microorganism containing a recombinant plasmid providing expression of the salmon growth hormone, the improvement in which comprises:
   1) transforming an *E. coli* strain with the plasmid ptrp 322 HSGH, said plasmid being described in FIG. 6;
   2) culturing the transformed bacteria obtained in step (1) in LB medium containing an effective amount of ampicillin to prevent the growth of bacteria lacking the ptrp 322 HSGH plasmid;
   3) diluting the culture of step (2) in medium;
   4) adding to the culture of step (3) indole acrylic acid and continuing the culture; and
   5) separating the bacteria from the culture medium and collecting the salmon growth hormone from within the bacteria, whereby said salmon growth hormone is obtained in a yield of 20% or greater of total *E. coli* protein.

4. The process of claim 3, wherein the *E. coli* strain that is transformed is W3110.

* * * * *